(12) United States Patent
Shimonaka

(10) Patent No.: US 8,796,039 B2
(45) Date of Patent: Aug. 5, 2014

(54) METHOD FOR MEASURING INHIBITORY ACTIVITY ON LIGAND-RECEPTOR BINDING

(75) Inventor: Yasushi Shimonaka, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 645 days.

(21) Appl. No.: 12/672,237

(22) PCT Filed: Aug. 6, 2008

(86) PCT No.: PCT/JP2008/064091
§ 371 (c)(1),
(2), (4) Date: Feb. 4, 2010

(87) PCT Pub. No.: WO2009/020142
PCT Pub. Date: Feb. 12, 2009

(65) Prior Publication Data
US 2011/0207233 A1    Aug. 25, 2011

(30) Foreign Application Priority Data
Aug. 6, 2007 (JP) ................. 2007-204303

(51) Int. Cl.
*G01N 33/543* (2006.01)
*G01N 33/68* (2006.01)
*G01N 33/566* (2006.01)
*G01N 33/74* (2006.01)

(52) U.S. Cl.
CPC .......... *G01N 33/566* (2013.01); *G01N 33/6854* (2013.01); *G01N 2500/00* (2013.01); *G01N 33/746* (2013.01); *G01N 33/54353* (2013.01)
USPC ............ 436/518; 435/7.1; 435/7.92; 436/501

(58) Field of Classification Search
None
See application file for complete search history.

(56) References Cited

U.S. PATENT DOCUMENTS

| 5,501,955 | A | 3/1996 | Bergman |
| 5,814,461 | A | 9/1998 | Bergmann et al. |
| 6,844,162 | B1 * | 1/2005 | Smith et al. ............ 435/7.1 |
| 2009/0203036 | A1 * | 8/2009 | Smith et al. ............ 435/7.1 |

FOREIGN PATENT DOCUMENTS

| JP | 6-501103 | 2/1994 |
| JP | 9-500215 | 1/1997 |
| JP | 2003-177131 | 6/2003 |
| WO | WO-99/64865 | 12/1999 |

OTHER PUBLICATIONS

D'Andrea et al., Anti-Erythropoietin Receptor (EPO-R) Monoclonal Antibodies Inhibit Erythropoietin Binding and Neutralizae Bioactivity, Blood, vol. 82, No. 1, 1993, pp. 46-52.*
Minich et al., A coated tube assay for the detectin of blocking thyrotropin receptor autoantibodies, The Journal of Clinical endocrinology& Metabolism, 89(1), 2004, pp. 352-356.*
Yanbin Yu et al., "A novel method for detecting neutralizing antibodies against therapeutic proteins by measuring gene expression", Journal of Immunological Methods 316 (2006) 8-17.
Nicole Casadevall et al., "Pure Red-Cell Aplasia and Antierythropoietin Antibodies in Patients Treated With Recombinant Erythropoietin", The New England Journal of Medicine, vol. 346, No. 7, Feb. 14, 2002, pp. 469-475.
Richard Tracey et al., "The detection of anti-erythropoietin antibodies in human serum and plasma Part I. Validation of the protocol for a radioimmunoprecipitation assay", Journal of Immunological Methods 283 (2003) 317-329.
Marian Kelley et al., "The detection of anti-erythropoietin antibodies in human serum and plasma Part II. Validation of a semi-quantitative 3H-thymidine uptake assay for neutralizing antibodies", Journal of Immunological Methods, 300 (2005) 179-191.
Robin Thorpe et al., "Assays for detecting and diagnosing antibody-mediated pure red cell aplasia (PRCA): An assessment of available procedures", Nephrology Dialysis Transportation, (2005) 20 [Suppl 4]: iv16-iv22.
International Search Report PCT/JP2008/064091 dated Oct. 21, 2008.
John Ferbas et al., "Feasibility of a Multiplex Flow Cytometric Bead Immunoassoay for Detection of Anti-Epoetin Alfa Antibodies", Clinical and Vaccine Immunology, Sep. 2007, vol. 14, No. 9, pp. 1165-1172.
Stephanie Mason et al., "Validation of the BIACORE 3000 platform for detection of antibodies against erythropoietic agents in human serum samples", Current Medical Research and Opinion, vol. 19, No. 7, 2003, 651-659.
Supplementary European Search Report EP 08 79 2247 dated Jul. 9, 2010.

* cited by examiner

Primary Examiner — Gary W Counts
(74) Attorney, Agent, or Firm — Foley & Lardner LLP

(57) ABSTRACT

A method for measuring the presence or absence and/or strength of the inhibitory activity of a test substance on binding between a ligand and a receptor thereof, which comprises the following steps (1) to (3):

(1) immobilizing either of the test substance or the ligand on a solid support;

(2) contacting the test substance and the ligand for a given period of time in the presence or absence of the receptor for the ligand; and (3) comparing the level of binding between the test substance and the ligand in the presence and absence of the receptor.

8 Claims, 2 Drawing Sheets

A METHOD FOR MEASURING INHIBITORY ACTIVITY ON LIGAND-RECEPTOR BINDING

CROSS-REFERENCE TO RELATED PATENT APPLICATIONS

This application is a U.S. National Phase of PCT/JP2008/064091 filed Aug. 6, 2008, which claims priority from Japanese Patent Application No. 2007-204303 filed Aug. 6, 2007, which is incorporated herein by reference in it's entirety.

TECHNICAL FIELD

The present invention relates to a method for measuring the presence or absence and/or strength of the inhibitory activity of a test substance on binding between a ligand and a receptor thereof. The method of the present invention is particularly useful as a highly sensitive and a simple method for detection of neutralizing activity.

BACKGROUND ART

When the body is repeatedly administered with a drug, such repeated administration may raise an antibody against this drug. Even in the case of recombinant drugs whose amino acid sequences are the same as those of endogenous substances, there is a possibility of raising autoantibodies, some of which may neutralize the original endogenous substances.

For example, in the case of recombinant human erythropoietin (rhEPO), some of the renal failure patients receiving EPO have been found to develop a neutralizing antibody against rhEPO although such cases are very rare, and it has also been reported that this antibody causes anti-EPO antibody-positive pure red cell aplasia (PRCA) as a complication in some patients (Non-patent Document 1).

Since the development of a neutralizing antibody against a drug not only eliminates the efficacy of the drug, but may also induce a new disease, it is important to detect such a neutralizing antibody in an early stage. However, conventional methods used for neutralizing antibody detection are not sufficient for this purpose. By way of example, for measurement of anti-EPO antibody, assays such as ELISA (Enzyme-Linked Immuno Sorbent Assay), RIP (radioactive immunoprecipitation) and bioassay have been used for neutralizing antibody measurement, but it is pointed out that these conventional methods used for neutralizing antibody detection are not sufficient in terms of detection sensitivity and/or complicated procedures (Non-patent Documents 2, 3 and 4). Moreover, antibodies against drugs are produced in very low concentrations in the body, and hence it has been very difficult to determine whether these antibodies are neutralizing antibodies.

For these reasons, once antibody production against a drug has been confirmed, drug administration must be stopped in some cases due to reasons of safety, regardless of whether this antibody has neutralizing activity. Thus, there has been a demand for a highly sensitive and a simple method for detection of neutralizing activity.

Non-patent Document 1: N Engl J. Med. 2002 Feb. 14; 346(7):469-75.
Non-patent Document 2: Journal of Immunological Methods 283 (2003)317-329
Non-patent Document 3: Journal of Immunological Methods 300 (2005)179-191
Non-patent Document 4: Nephrol Dial Transplant (2005) 20[Suppl 4]:iv 16-22

DISCLOSURE OF THE INVENTION

Problems to be Solved by the Invention

The present invention was made under such circumstances and aims to provide a method for measuring the presence or absence and/or strength of the inhibitory activity of a test substance on binding between a ligand and a receptor thereof, which method can be used for highly sensitive and simple detection of neutralizing antibodies.

Means for Solving the Problems

As a result of extensive and intensive efforts made to achieve the above aim, the inventors of the present invention have found that either of a test substance or a ligand is pre-immobilized on a solid support and the level of binding between the test substance and the ligand is compared in the presence or absence of a receptor for the ligand, whereby inhibited binding between the ligand and the receptor can be detected with high sensitivity. This finding led to the completion of the present invention.

Namely, the present invention more specifically provides [1] to [5] shown below.
[1] A method for measuring the presence or absence and/or strength of the inhibitory activity of a test substance on binding between a ligand and a receptor thereof, which comprises the following steps (1) to (3):
(1) immobilizing either of the test substance or the ligand on a solid support;
(2) contacting the test substance and the ligand for a given period of time in the presence or absence of the receptor for the ligand; and
(3) comparing the level of binding between the test substance and the ligand in the presence and absence of the receptor.
[2] The method according to [1] above, wherein the test substance is an antibody.
[3] The method according to [1] or [2] above, wherein the level of binding between the test substance and the ligand is measured by a method used to detect intermolecular physical binding.
[4] The method according to any one of [1] to [3] above, wherein the ligand is a drug administered to a patient, and the test substance is an antibody collected from the patient.
[5] The method according to any one of [1] to [4] above, wherein the ligand is erythropoietin, the receptor is an erythropoietin receptor, and the test substance is an anti-erythropoietin antibody.
[6] A method for detecting the presence or absence and/or strength of the neutralizing activity of a test substance on a ligand, which comprises the method according to any one of [1] to [5] above.

Advantages of the Invention

The present invention is directed to a novel method which allows simple detection of inhibited binding between ligand and receptor even when a target to be tested is in a low concentration. Moreover, since this method can confirm inhibited binding between ligand and receptor even when a target to be tested is in a low concentration, it is possible to detect, with high sensitivity, a neutralizing antibody against a drug produced in the body of a patient receiving repeated administration of the drug. To confirm whether a test antibody has neutralizing activity by using a conventional method for detecting a neutralizing antibody against EPO (i.e., a bioassay-based method for neutralizing antibody detection described later in Comparative Example 2), the antibody is required in an amount of at least 650 ng/mL, calculated as the concentration in serum. In contrast, in the detection method of the present invention, an antibody concentration of 40 ng/mL is sufficient to detect an antibody having neutralizing activity. The method of the present invention enables the early detection of neutralizing antibody development and also allows proper administration of drugs.

The present invention will be further described in more detail by way of the following examples, which are provided for illustrative purposes only and are not intended to limit the scope of the invention.

MODE FOR CARRYING OUT THE INVENTION

Definition of Terms

Figure 1:
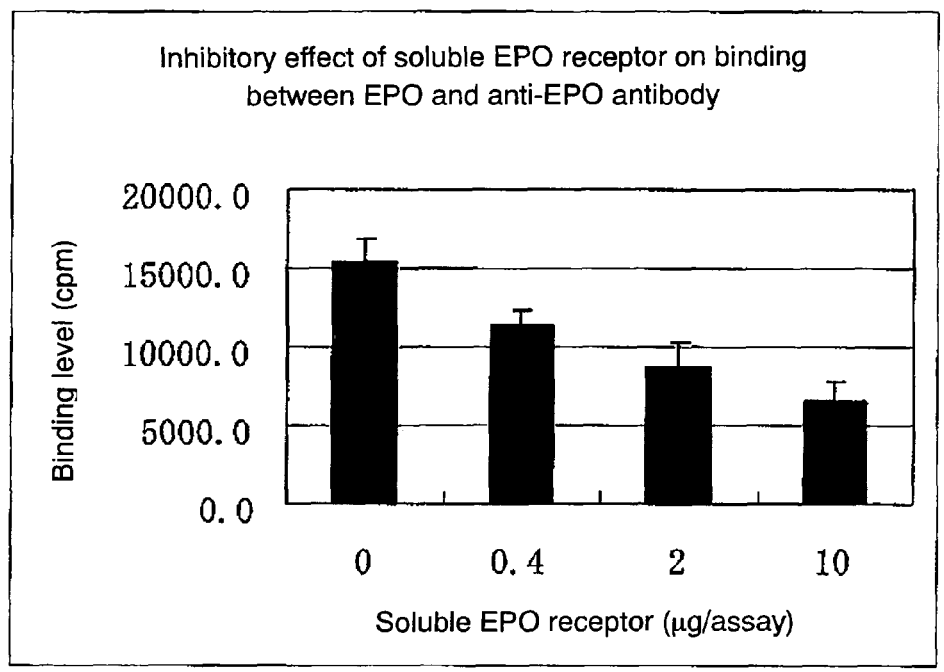
FIG. 1 is a graph showing the effect of sEPOR (soluble EPO receptor) at different concentrations on binding between anti-EPO antibody and EPO.

As used herein, the term "test substance" is not limited in any way and preferably refers to a substance which is contained in plasma, serum, blood, tear, body fluid or the like collected from a target receiving drug administration, and particularly preferably refers to an antibody.

As used herein, the term "ligand" is not limited in any way as long as it refers to a substance which binds to a receptor in the body and thereby promotes or inhibits signal transduction into cells. The ligand of the present invention is preferably a drug having the above action, for example, a recombinant drug of an endogenous protein or an antibody. Examples include cytokines such as EPO, G-CSF and interferon, as well as antibody drugs.

As used herein, the term "receptor" is intended to mean a structure which binds to the "ligand" of the present invention and thereby causes cellular responses, or alternatively, a structure which is a fragment of the above structure and has at least a binding site for the "ligand." When the "ligand" is a cytokine such as EPO, G-CSF or interferon, examples include a receptor of this cytokine or a fragment of this receptor (i.e., a receptor fragment having at least a binding site for the "ligand" such as an extracellular region of the receptor). Likewise, when the "ligand" is an antibody drug, examples include an antigen to which this antibody binds or an antigen fragment having an antibody-binding site of the antigen.

In the present invention, commonly used immobilization techniques can be used for "immobilization on a solid support." For example, when the test substance is an antibody, the antibody can be immobilized on a solid support by using Protein G. Other techniques for immobilization on a solid support include those using sodium carbonate buffer, those using chemical crosslinking (e.g., amino coupling), and those using biotin-avidin binding. The solid support used for this purpose is not limited in any way and includes carrier particles, microtiter plates, test tubes, etc. In the Example section described later, anti-EPO antibody was immobilized on commercially available Protein G Sepharose 4FF (GE Healthcare Bio-Sciences KK).

As used herein, the phrase "method used to detect intermolecular physical binding" may refer to any method which allows detection of intermolecular physical binding, and examples include RIP assay, SPR (surface plasmon resonance) assay, bioassay, ELISA assay, etc. Experimental procedures for these assays are known to those skilled in the art.

Measurement Method of the Present Invention

In one embodiment for implementing the present invention, when a test substance is immobilized on a solid support, inhibited binding between ligand and receptor can be detected, for example, by using RIP assay. The test substance is immobilized on a solid support and allowed to come in contact with a ligand labeled with a radioisotope or a fluorescent dye in the presence or absence of a receptor for the ligand to detect the ligand bound to the test substance, thereby making it possible to determine whether the test substance inhibits the binding between the ligand and the receptor. If the binding between the test substance and the ligand is lower in the presence of the receptor than in the absence of the receptor, this test substance can be determined to have inhibitory activity on ligand-receptor binding. More specifically, the present invention can be implemented according to the procedures described later in the Example section. Namely, $^{125}$I-labeled EPO and various concentrations of soluble EPO receptor were mixed in RIA tubes. To the samples thus prepared (the receptor groups) and a sample free from soluble EPO receptor (the receptor-free group), human serum and anti-EPO antibody were added as a test sample of human serum containing anti-EPO antibody. A suspension of Protein G Sepharose 4FF was then added to each tube and vortexed to immobilize the anti-EPO antibody on the solid support, followed by centrifugation to remove the supernatant. The levels of radioactivity (cpm) in the resulting sediment and background were measured for each sample with a gamma counter. This method was actually used to determine the level of radioactivity in analytes, indicating that the binding between anti-EPO antibody and $^{125}$I-EPO was inhibited in a manner dependent on the dose of soluble EPO receptor.

In another embodiment for implementing the present invention, when a ligand is immobilized on a solid support, the immobilized ligand is allowed to come in contact with a test substance in the presence or absence of a receptor for the ligand to detect the test substance bound to the immobilized ligand, thereby making it possible to determine whether the test substance inhibits the binding between the ligand and the receptor. As in the case above, if the binding between the test substance and the ligand is lower in the presence of the receptor than in the absence of the receptor, this test substance can be determined to have inhibitory activity on ligand-receptor binding.

Measurement of the Presence or Absence of Neutralizing Activity

According to the above measurement, a substance having inhibitory activity on ligand-receptor binding can be determined to have neutralizing activity on the ligand. For example, this measurement method can be used to determine whether a patient receiving drug administration produces a neutralizing antibody against the drug.

EXAMPLES

Example 1

Effect of sEPOR (Soluble EPO Receptor) at Different Concentrations on Binding Between Anti-EPO Antibody and $^{125}$I-EPO A $^{125}$ I-EPO solution (50 μL, 190822 cpm) diluted with analyte diluent (10 mmol/L Tris-HCl buffer containing 150 mmol/L NaCl, 0.02% NaN$_3$, 0.1% BSA and 0.1 vol % Tween 20™, pH 7.4) and sEPOR (50 μL, R&D Systems) diluted to 0, 8, 40 or 200 μg/mL with the same analyte diluent were mixed in RIA tubes and allowed to stand overnight (about 20 hours) at about 4° C. The experiment was performed in triplicate for each condition.

To each tube, human pooled serum (20 μL, Gemini Bio-Products) and anti-EPO antibody (80 μL) diluted to 100 ng/mL with the analyte diluent were added and vortexed (200 μL in total) and allowed to stand at about 4° C. for 6 hours.

A suspension of Protein G Sepharose 4FF (50 μL) was added to each tube and vortexed in a shaker at room temperature for 1 hour. It should be noted that the suspension of Protein G Sepharose 4FF was prepared by repeating twice the procedure of suspending Protein G Sepharose 4FF (GE Healthcare Bio-Sciences KK) in an equal volume of the analyte diluent and centrifuging the resulting suspension (1660× G, about 4° C., 1 minute) to remove the supernatant, followed by addition of 1 mL analyte diluent per gram wet weight of the gel (allowable range: ±2%) to suspend the gel. Next, the cooled analyte diluent (2 mL) was added to each tube and vortexed, followed by centrifugation (1660×G, about 4° C., 5 minutes) to remove the supernatant. This sediment was diluted again with the cooled analyte diluent (2 mL) and vortexed, followed by centrifugation (1660×G, about 4° C., 5 minutes) to remove the supernatant. The levels of radioactivity (cpm) in the sediment and background (5 empty tubes) were measured for 5 minutes with a gamma counter (COBRA Quantum 5005 Gamma Counting system, PerkinElmer). The following equation was used to determine the level of radioactivity in each analyte.

Level of radioactivity (cpm) in analyte=Measured level of radioactivity in analyte (cpm)−Background level (cpm averaged from 5 empty tubes)

The results obtained are shown in FIG. 1. The binding between anti-EPO antibody and $^{125}$I-EPO was inhibited in a manner dependent on the dose of sEPOR.

Example 2

Study with serum samples from different humans

A $^{125}$I-EPO solution (50 μL, 88869 cpm) diluted with analyte diluent and the diluent alone (50 μL, Control) or sEPOR (50 μL) diluted to 40 μg/mL were mixed in RIA tubes and allowed to stand overnight (about 20 hours) at about 4° C. The experiment was performed in duplicate for each condition.

To the respective tubes, serum samples from different humans (20 μL, UNIGLOBE RESEARCH CORPORATION) and anti-EPO antibody (80 μL) diluted to 10 or 100 ng/mL with the analyte diluent were added and vortexed (200 μL in total) and allowed to stand at about 4° C. for 6 hours.

A suspension of Protein G Sepharose 4FF (50 μL) was added to each tube and vortexed in a shaker at room temperature for 1 hour. The cooled analyte diluent (2 mL) was added to each tube and vortexed, followed by centrifugation (1660× G, about 4° C., 5 minutes) to remove the supernatant. This sediment was diluted again with the cooled analyte diluent (2 mL) and vortexed, followed by centrifugation (1660×G, about 4° C., 5 minutes) to remove the supernatant. The levels of radioactivity (cpm) in the sediment and background (5 empty tubes) were measured for 5 minutes with a gamma counter (COBRA Quantum 5005 Gamma Counting system, PerkinElmer). The same procedure as used in Example 1 was repeated to determine the level of radioactivity in each analyte.

The results obtained are shown in Table 1. It should be noted that the antibody concentration is expressed as the concentration in serum.

TABLE 11

| Serum | Serum alone | | 40 ng/mL | | 400 ng/mL | |
|---|---|---|---|---|---|---|
| No. | Control | EPOR | Control | EPOR | Control | EPOR |
| 1 | 212.7 | 177.7 | 910.3 | 479.1 | 7867.6 | 3215.0 |
| 2 | 160.7 | 186.2 | 966.7 | 535.0 | 8032.0 | 3714.2 |
| 3 | 174.1 | 212.0 | 1054.2 | 539.4 | 8232.4 | 3443.8 |
| 4 | 144.1 | 200.3 | 960.9 | 498.6 | 7835.9 | 3521.6 |
| 5 | 640.2 | 287.4 | 1310.2 | 573.4 | 8195.5 | 3643.8 |
| 6 | 233.8 | 255.6 | 867.5 | 491.1 | 7609.1 | 3246.8 |
| 7 | 211.7 | 297.0 | 953.1 | 532.0 | 7684.8 | 3542.6 |
| 8 | 242.3 | 243.9 | 1030.7 | 563.3 | 8112.4 | 3528.5 |
| 9 | 357.4 | 442.1 | 1316.7 | 529.2 | 9368.0 | 3663.8 |
| 10 | 218.9 | 316.3 | 1125.3 | 621.2 | 8471.5 | 3904.0 |
| Average | 259.6 | 261.8 | 1049.5 | 536.2 | 8140.9 | 3542.4 |
| STD | 146.0 | 79.4 | 157.0 | 42.3 | 505.3 | 208.2 |

In all of the serum samples, inhibited binding between anti-EPO antibody and $^{125}$I-EPO was observed upon addition of sEPOR.

This result indicated that when using the method of the present invention, an antibody concentration of 40 ng/mL was sufficient to detect the inhibitory activity of a test antibody.

Comparative Example

1. Receptor Assay

Human erythroleukemia cell line AS-E2 was cultured in Iscove's modified Dulbecco's medium (IMDM) containing 20% FBS (Hyclone) in the presence of 10 ng/mL EPO in a CO$_2$ incubator at 37° C. under 5% CO$_2$ for 6 days. After completion of the culture, the cells were centrifuged at about 4° C. at 1000 rpm for 5 minutes, and the supernatant was removed by suction. The cells were washed three times with 20% FBS-containing IMDM and then cultured overnight (about 24 hours) in a CO$_2$ incubator at 37° C. under 5% CO$_2$.

After the culture, the cells were collected by centrifugation, washed twice with 1% BSA-containing Dulbecco's PBS (1% BSA/PBS), and then diluted to 1×10$^7$ cells/mL. To anti-EPO antibody (50 μL) diluted to 0, 0.46, 2.78, 16.7 or 100 μg/mL with 1% BSA/PBS, $^{125}$I-EPO (50 μL, 100025 cpm) was added and the cell suspension diluted above (200 μL) was further mixed, followed by standing overnight (about 20 hours) at about 4° C.

The cells after standing were centrifuged, washed twice with 1% BSA/PBS, and measured for their radioactivity level (cpm) with a gamma counter for 5 minutes.

The background level was measured in the same manner, except for using the cells in the presence of 2 μg non-labeled EPO in place of $^{125}$I-EPO and the antibody. Specific binding was calculated by subtracting the background radioactivity from the radioactivity at each antibody concentration.

Figure 2:
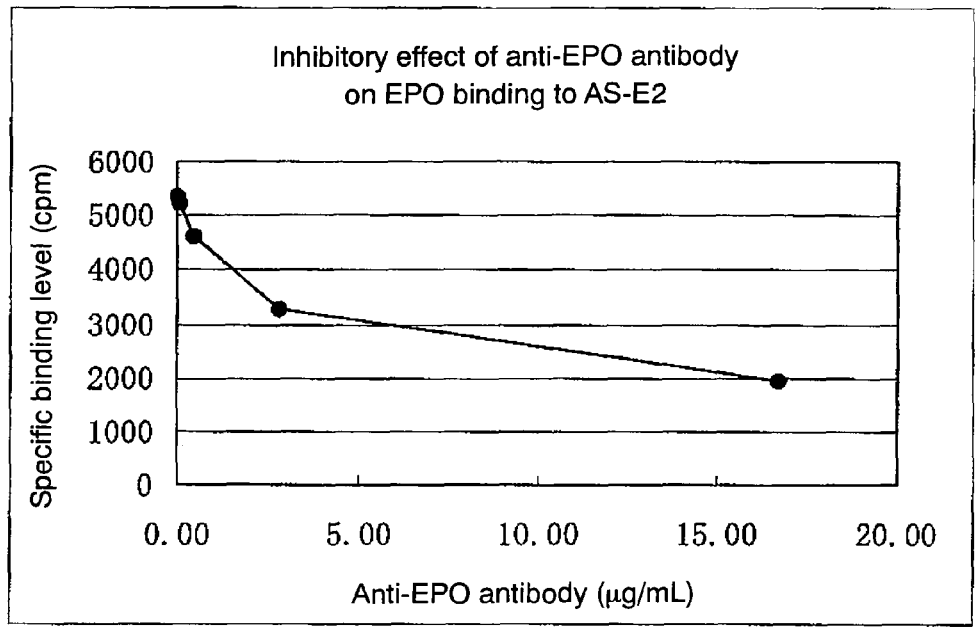
FIG. 2 is a graph showing the effect of anti-EPO antibody concentration on EPO binding, as measured by receptor assay using AS-E2 cells.

The results obtained are shown in FIG. 2. To confirm whether EPO binding onto the cell surface was inhibited, at least 500 ng/mL of antibody was required. For actual evaluation in a system containing 50% serum, an antibody concentration of 1 μg/mL (calculated as the concentration in serum) is required.

2. Bioassay

A suspension of AS-E2 cells, which had been cultured in 20% FBS/IMDM in the presence of 10 ng/mL EPO, was collected from culture flasks into centrifugal tubes, and centrifuged at 1000 rpm (about 240×G) for 10 minutes. After removal of the supernatant, the cells were suspended in test medium (20% FBS/IMDM), centrifuged again to remove the supernatant, and then suspended in the test medium. This procedure was repeated three times to remove EPO remaining in the medium. An aliquot of the cell suspension was stained with 0.4% trypan blue and counted to determine the number of living cells and the survival rate. The cell suspension was diluted with the test medium to contain living cells at $2 \times 10^5$ cells/mL.

An EPO solution diluted with the test medium was dispensed in a volume of 40 μL/well in a 96-well microplate. Further, a sample or the test medium was added in a volume of 10 μL/well. Three wells were used for each sample (triplicate assay). The plate was transferred to a $CO_2$ incubator and allowed to stand for 30 to 60 minutes. The plate was removed from the $CO_2$ incubator, and the cell suspension of $2 \times 10^5$ cells/mL was added to all test wells in a volume of $1 \times 10^4$ cells/50 μL/well. Independently of these wells, another three wells (blank wells) were provided, in which the cells were not seeded. To these blank wells, the test medium was added in a volume of 100 μL/well. The plate was incubated in a $CO_2$ incubator for 96 to 97 hours. To minimize drying of the wells in the plate, PBS was added in a volume of 300 μL/well to wells containing nothing (empty wells).

After completion of the culture, a WST-1 solution was added to and mixed in all of the wells in a volume of 10 mL/well, and the absorbance at 450 nm (0 hour) was measured for each well with a microplate reader using a control wavelength of 620 nm. After incubation in a $CO_2$ incubator for 2 hours, the absorbance at 450 nm (2 hour) was measured for each well using a control wavelength of 620 nm.

Figure 3:
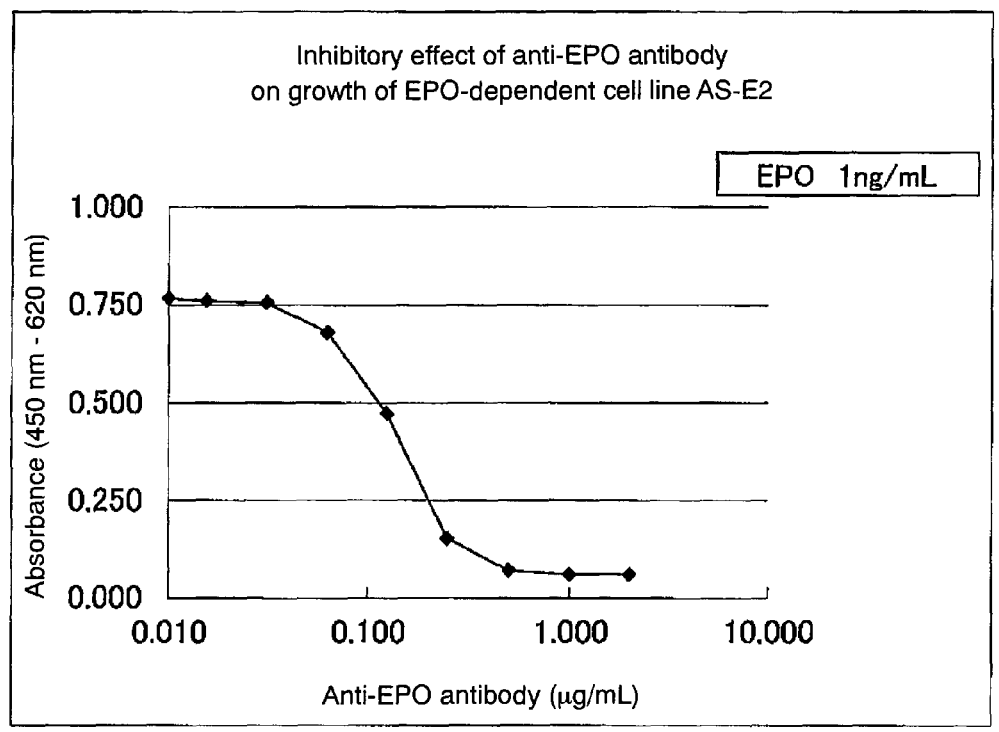
FIG. 3 is a graph showing the effect of anti-EPO antibody concentration on EPO binding, as measured by bioassay using AS-E2 cells.

The results obtained are shown in FIG. 3.

In this system, growth inhibition could be confirmed at a test antibody concentration of 130 ng/mL or more. Since the upper limit for the concentration of serum added to cell systems is 20%, in the case of preparing a system containing 20% serum, the presence of a neutralizing antibody can be detected if the serum concentration of the neutralizing antibody is 650 ng/mL or more.

In general, in evaluation systems using cell lines, addition of a large amount of human serum is known to cause non-specific growth inhibition. Thus, to detect specific growth inhibition as intended here, human serum to be added is often set within 20%. This system therefore requires 650 ng/mL of antibody to perform a growth inhibition test.

The invention claimed is:

1. A method for detecting a test substance in a body fluid sample, comprising
    (1) immobilizing either a test substance or a ligand on a solid support;
    (2) contacting the test substance, which is contained in the body fluid sample, and the ligand for a given period of time in the presence and absence of a receptor for the ligand, wherein the test substance is an antibody against the ligand;
    (3) detecting the binding between the test substance and the ligand; and
    (4) comparing the level of binding between the test substance and the ligand in the presence and absence of the receptor, wherein the test substance has an inhibitory activity on binding between the ligand and the receptor if the level of binding between the test substance and the ligand in the presence of the receptor is lower than the level of binding between the test substance and the ligand in the absence of the receptor.

2. The method according to claim 1, wherein the level of binding between the test substance and the ligand is measured by a method used to detect intermolecular physical binding.

3. The method according to claim 1, wherein the ligand is a drug administered to a patient, and the test substance is an antibody collected from the patient.

4. The method according to claim 1, wherein the ligand is erythropoietin, the receptor is an erythropoietin receptor, and the test substance is an anti-erythropoietin antibody.

5. The method according to claim 1, further comprising correlating the presence or absence of the inhibitory activity of the test substance on binding between the ligand and the receptor to the presence or absence of a neutralizing activity of the test substance on the ligand, wherein the test substance has the neutralizing activity on the ligand if the test substance has the inhibitory activity on binding between the ligand and the receptor.

6. The method according to claim 1, wherein the body fluid is serum of a patient, and wherein the ligand is a drug administered to said patient.

7. The method according to claim 6, wherein the ligand is labelled with a radioisotope of fluorescent dye.

8. The method according to claim 4, wherein the method is capable of detecting anti-erythropoietin neutralizing antibodies at a serum concentration of 40 ng/mL.

* * * * *